United States Patent [19]

Ledig, deceased et al.

[11] 4,233,445
[45] Nov. 11, 1980

[54] 7-(SUBSTITUTED)-7H-PYRROLO[3.2-f]-QUINAZOLINE-1,3-DIAMINES

[75] Inventors: Kurt W. Ledig, deceased, late of Philadelphia, Pa.; by David R. Howes, Executor, Baltimore, Md.

[73] Assignee: American Home Products Corporation, New York, N.Y.

[21] Appl. No.: 54,737

[22] Filed: Jul. 5, 1979

Related U.S. Application Data

[62] Division of Ser. No. 920,083, Jun. 28, 1978.

[51] Int. Cl.$^2$ ............................................ C07D 487/04
[52] U.S. Cl. .................................................. 544/250
[58] Field of Search ......................... 544/250; 424/251

[56] References Cited

U.S. PATENT DOCUMENTS

| | | | |
|---|---|---|---|
| 2,945,859 | 7/1960 | Hitchings et al. | 544/249 |
| 3,505,330 | 4/1970 | Davoll et al. | 544/291 |
| 4,118,561 | 10/1978 | Ledig | 542/470 |

OTHER PUBLICATIONS

DeGraw, et al., J. Med. Chem., vol. 17, pp. 762–764 (1974).
Davoll, et al., J. Med. Chem., vol. 15, pp. 812–826 (1972).
Elslager, et al., J. Med. Chem, vol. 15, pp. 1138–1146 (1972).
Elslager, Progress in Drug Research, vol. 18, pp. 99–172 (1974).
Reed, et al., Amer. J. Hyg., vol. 27, pp. 493–497 (1938).

*Primary Examiner*—Donald G. Daus
*Assistant Examiner*—Diana G. Rivers
*Attorney, Agent, or Firm*—George Tarnowski

[57] ABSTRACT

7-(Substituted)-pyrrolo[3,2-f]quinazoline-1,3-diamines possess antibacterial activity in vitro. The invention also provides compounds having synergism in vivo with sulfa drugs against bacterial infections.

3 Claims, No Drawings

7-(SUBSTITUTED)-7H-PYRROLO[3,2-f]-QUINAZOLINE-1,3-DIAMINES

This is a division of application Ser. No. 920,083, filed June 28, 1978.

Various derivatives of 2,4-diaminoquinazoline and 2,4,6-triaminoquinazoline are described in the literature and are known to possess antifolic activity in bacterial systems. Such compounds are also known to exhibit antibacterial or antiprotozoal activity. For example, 2,4-diaminoquinazolines having an alkyl group at the 5-position and/or 6-position or having a trimethylene bridge between the 5- and 6-position possess antibacterial activity [see Hitchings et al., U.S. Pat. No. 2,945,859 or De Graw et al., J. Med. Chem., 17, 762 (1974)]. 2,4-Diamino-6-[(arylmethyl)amino]-quinazolines; 2,4-diamino-6-{[(substituted aryl)methyl]amino}-quinazolines; and 2,4-diamino-6-{[(heterocyclic)methyl]amino}-quinazolines along with derivatives having a 5-alkyl substituent or N6-alkyl substituent exhibit antimalarial activity. [See Davoll et al., J. Med. Chem., 15, 812 (1972); Elslager et al., J. Med. Chem., 15, 1138 (1972); see also the review article by E. Elslager entitled, "New Perspectives on the Chemotherapy of Malaria, Filariasis, and Leprosy", Progress in Drug Research 18, 99-172 (1974), in particular pages 111-116 and 152-154].

The pyrrolo[3,2-f]quinazoline-1,3-diamines of the invention differ from the known 2,4,6-triaminoquinazolines in that the 5-position and the $N^6$ position of the latter are bridged by an ethylene moiety thus forming a novel tricyclic heterocycle.

The invention sought to be patented comprises compounds of the formula:

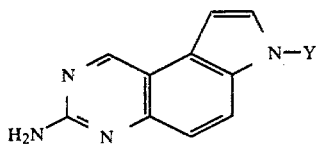

or a non-toxic acid addition salt thereof, wherein:
Y is —CH$_2$R or —R$^1$
wherein:
R is 2,4-dichlorophenyl, 3-acetylphenyl, 3-carbomethoxyphenyl, 3-isopropylphenyl, 4-carboisopropyloxyphenyl, 4-carbo-2-pentyloxyphenyl, 4-carbomethoxyphenyl, or 4-hydroxyphenyl;
and
R$^1$ is 4-pyridinyl, 2-(4-methylpyridinyl), 4-trifluoromethylphenyl, or 4-carbamoylphenyl.

The compounds of Formula I, wherein Y, R, and R$^1$ are as hereinbefore defined or the salts thereof, inhibit the growth of bacteria in vitro as demonstrated in a standard tube dilution test employing seed agar or Wellcotest Sensitivity Test Agar fortified with 5% hemolyzed horse blood as the growth medium. The compounds have shown activity in vitro against one or more of the following strains of bacteria: *S. aureus* Smith, *S. aureus* 53-180, *N. catarrhalis* 8193, *E. coli* 9637, *S. paratyphi* 11737, *K. pneumoniae* 10031, or *P. vulgaris* 6896.

The invention also provides compounds which will potentiate the antibacterial effects of sulfa drugs. When tested by the oral route of administration in mice, 7-(4-pyridinyl)-7H-pyrrolo[3,2-f]-quinazoline-1,3-diamine gave a synergistic effect with sulfamethoxazole against bacterial infections.

In general, the compounds of Formula I having an N$^7$-substituent are prepared by reacting 7-H-pyrrolo[3,2-f]quinazoline-1,3-diamine with an alkali metal base to form the corresponding alkali metal salt, and the salt is reacted with the appropriate reagent, RCH$_2$—Z or R$^1$—Z, in order to attach the desired substituent, RCH$_2$— or R$^1$—, at the 7-position. The base employed in the first step must be of sufficient strength to remove the proton from the indolic nitrogen of the starting material. Examples of such bases are sodium and potassium hydride, potassium t-butoxide, and lithium or potassium amide.

In the reagents RCH$_2$—Z or R$^1$—Z, R and R$^1$ are as defined hereinbefore with respect to Formula I (except that R and R$^1$ cannot be a group which contains a free hydroxyl group as a substituent) and Z is a leaving group.

When the reagent is RCH$_2$—Z, the preferred leaving group Z is a chlorine, bromine, or iodine atom. When the reagent is R$^1$—Z, the preferred leaving group is a fluorine, bromine, chlorine, or iodine atom. Other examples, of appropriate leaving groups (Z) for RCH$_2$—Z are tosyloxy or mesyloxy. The reaction is conveniently carried out in an inert solvent, such as dimethylformamide (DMF) or dimethylacetamide (DMA). In a preferred method, the 7-H-pyrrolo[3,2-f]quinazoline-1,3-diamine is treated with sodium-hydride in dimethylformamide and the appropriate reagent (RCH$_2$—Z or R$^1$—Z) is added to the reaction mixture. In the reaction employing the reagent R$^1$—Z, it is preferred to heat the reaction mixture at a temperature above 50° C.

7-H-Pyrrolo[3,2-f]quinazoline-1,3-diamine is prepared by heating an acid addition salt of 5-aminoindole at a temperature of about 185°-215° C. with an alkali metal dicyanamide, such as sodium or potassium dicyanamide, in an aliphatic alcohol solvent. Best results are achieved if a >2:1 molar ratio of the dicyanamide to the 5-aminoindole acid addition salt is employed. A molar ratio of about 2.5:1 is preferred. The reaction is conveniently carried out by heating the reactants at the reflux temperature of the solvent. Aliphatic alcohols having a boiling point of about 185° C. to about 215° C. are preferred solvents. In a preferred method, the 5-aminoindole acid addition salt is heated at reflux temperature in 1-octyl alcohol with sodium dicyanamide until the reaction is complete.

When it is desired to prepare a compound of Formula I wherein —CH$_2$—R or R$^1$ contain a free aromatic hydroxy group, such compound can be conveniently prepared by cleavage of a corresponding aromatic methoxy compound. For example, 7-[(4-hydroxyphenyl)-methyl]-7H-pyrrolo[3,2-f]quinazoline-1,3-diamine is prepared by cleaving 7-[(4-methoxyphenyl)methyl]-7H-pyrrolo-[3,2-f]quinazoline-1,3-diamine in the presence of boron tribromide.

The starting materials which are 5-aminoindole and the reagents RCH$_2$—Z and R$^1$—Z are either known compounds or can be prepared by known methods for analogous compounds or by obvious modifications of the known methods.

The compounds of Formula I may be isolated and purified either in the form of the free bases or the acid addition salts. Methods for converting one such form to another will be obvious to one skilled in the art of chemistry.

For pharmacological use, the compounds of Formula I may be administered in the form of an acid addition salt of a non-toxic organic or inorganic acid. The salts may be prepared by methods well known in the art. Appropriate salts are those formed from the following acids: hydrochloric, hydrobromic, maleic, benzoic, pamoic, methanesulfonic, or acetic.

For pharmacological use, the compounds of Formula I may be administered alone or in combination with pharmaceutically acceptable carriers, the proportion and nature of which are determined by the solubility and chemical properties of the compound selected, the chosen route of administration, and standard pharmaceutical practice. For example, the compounds of Formula I may be administered orally in solid dosage forms, e.g. capsules, tablets, or powders, or in liquid forms, e.g. solutions or suspensions. The compounds may also be injected parenterally in the form of sterile solutions or suspensions. Solid oral forms may contain conventional excipients, for instance: lactose, succrose, magnesium stearate, resins, and like materials. Liquid oral forms may contain various flavoring, coloring, preserving, stabilizing, solubilizing or suspending agents. Parenteral preparations are sterile aqueous or non-aqueous solutions or suspensions which may contain various preserving, stabilizing, buffering, solubilizing, or suspending agents. If desired, additives, such as saline or glucose may be added to make the solutions isotonic.

The following examples are illustrative of the methods of making and using the compounds of the invention. All temperatures are in centigrade.

EXAMPLE 1

7-H-Pyrrolo[3,2-f]quinazoline-1,3-diamine

A suspension of 168.6 g. 5-aminoindole hydrochloride (prepared by treating a methanolic suspension of 5-aminoindole with excess isopropanolic hydrogen chloride and diluting the salt solution with ether), 222 g. sodium dicyanamide (previously recrystallized from methanol), and 3 l. 1-octanol are refluxed with thorough stirring (under nitrogen) for 13 hours, and the hot mixture is filtered. The insolubles are washed with 500 ml. hot 1-octanol; the combined filtrates are diluted with an equal volume of ether and are acidified to pH 1 with isopropanolic hydrogen chloride. A fine, yellow precipitate is collected by filtration (slow) and is dissolved in 3 l. warm water. The aqueous solution is filtered through a coarse, sintered glass funnel. Upon cooling to ca. 25° C., the solution is washed with ethyl acetate and with ether. Basification of the solution with aqueous sodium hydroxide affords a yellow precipitate which is collected, thoroughly washed with water and dried to constant weight. The crude product (141.5 g.) is dissolved in ca. 10 l. methanol, treated with charcoal, and filtered thru Celite. The methanolic solution is concentrated to a volume of ca. 400 ml., diluted with 200 ml. acetone and chilled.

The solid that separates is washed with cold acetone and is dried to provide 77.6 g. of the title compound, m.p. 263°-265° (dec.). An additional 17.2 g. of product [m.p. 262°-264° (dec.)] are isolated by concentrating the crystallization mother liquor to a volume of ca. 40 ml., adding 40 ml. acetone, and chilling. Recrystallization of a 1.0 g. quantity of product [m.p. 263°-265° (dec.)] from methanol-acetone gives 395 mg. title compound, m.p. 264° (dec.); NMR (dDMSO): δ 7.14 (doublet, J=3 Hz, 9$\underline{H}$), 7.20 (doublet, J=9 Hz, 5 or 6$\underline{H}$), 7.54 (doublet, J=3 Hz, 8$\underline{H}$), 7.78 (doublet, J=9 Hz, 5 or 6$\underline{H}$), 11.65 (broad singlet, exchangeable, 7$\underline{H}$) p.p.m.; $\lambda_{max}^{95\% \ EtOH}$ 232.5 (ε 24,300), 258 (ε 22,120), 312 (ε 8,090), 340.5 (ε 7,420) nm; $\lambda_{min}^{95\% \ EtOH}$ 250 (ε 20,940), 279 (ε 2,310), 330 (ε 7,140) nm.

7-$\underline{H}$-Pyrrolo[3,2-f]quinazoline-1,3-diamine (5.62 g. prepared in a manner similar to that described above) in 300 ml. methanol is treated with excess isopropanolic hydrogen chloride, and the solution is concentrated to a volume of ca. 100 ml., diluted with 200 ml. dimethoxyethane, and thoroughly cooled. The salt is collected and dried. Weight 2.7 g. Concentration of the mother liquor provides an additional 3.8 g. salt. Recrystallization of the two solids from methanol-ethanol yields 5.26 g. title compound as the monohydrochloride salt m.p. >310°.

Analysis for: $C_{10}H_9N_5 \cdot HCl$. Calculated: C, 50.96; H, 4.28; N, 29,72; Cl, 15.05. Found: C, 50.81; H, 4.22; N, 30.01; Cl, 14.88.

Employing conditions similar to those above, A. Rosowsky and N. Papathanasopoulos [J. Org. Chem., 39, 3293 (1974)] converted naphthylamines into 2,4-diaminobenzo[h]quinazolines.

EXAMPLE 2

7-[(2,4-Dichlorophenyl)methyl]-7$\underline{H}$-pyrrolo[3,2-f]quinazoline-1,3-diamine A suspension of 7.97 g. of 7-$\underline{H}$-pyrrolo[3,2-f]quinazoline-1,3-diamine in 500 ml. of dry dimethylformamide is stirred under nitrogen as 4.61 g. of ca. 50% sodium hydride-mineral oil dispersion is added carefully. After stirring for 1.5 hours, a solution of 8.99 g. of 2,4-dichlorobenzyl chloride in 30 ml. of dry dimethylformamide is added during ca. 10 minutes. Stirring is continued for 5 hours and then 25 ml. of glacial acetic acid is added to the reaction mixture. After removal of solvent (in vacuo), the residue is stirred throughly with a mixture of excess aqueous potassium carbonate solution and 100 ml. of 1 N sodium hydroxide solution and filtered. The crude product is dissolved in 5 liters of boiling methanol, treated with charcoal, and filtered through Celite. The filtrate is concentrated to ca. 500 ml. and chilled. The crystalline solid is collected and again recrystallized from methanol to afford 6.33 g. of the title compound, m.p. 249°-250° C., NMR (dDMSO and D$_2$O): δ 5.58 (singlet, N—C$\underline{H}_2$—C$_6$H$_3$Cl$_2$), 6.68 (doublet, J=8 Hz, 5$\underline{H}$), 7.10 (doublet, J=3 Hz, 9$\underline{H}$), 7.52 (doublet, J=3 Hz, 8$\underline{H}$), 7.68 (doublet, J=8 Hz, 6$\underline{H}$) p.p.m.; $\lambda_{max}^{95\% \ EtOH}$ 258 mμ (26,000) and 315 mμ (8,500).

Analysis for: $C_{17}H_{13}N_5Cl_2$. Calculated: C, 57.00; H, 3.66; N, 19.55; Cl, 19.80. Found: C, 56.97; H, 3.75; N, 19.63; Cl, 18.85.

EXAMPLES 3-8

Employing conditions similar to those recorded in Example 2, 7$\underline{H}$-pyrrolo[3,2-f]quinazoline-1,3-diamine, in dimethylformamide, is converted to the Nind-sodium salt with ca. 50% sodium hydride-mineral oil dispersion and the salt is reacted with the indicated halide for the specified period to provide the 7-(substituted)methyl-7-H-pyrrolo[3,2-f]quinazoline-1,3-diamines described in Table I.

TABLE I

7-(Substituted)-7-H-pyrrolo[3,2-f]quinazoline-1,3-diamines

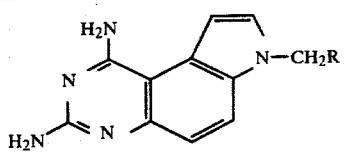

| Example No. | R | Alkylating Agent | Reax. Time (hours) | Recryst. Solv. | m.p., °C. |
|---|---|---|---|---|---|
| 3 | 3-acetylphenyl | 3-acetylbenzyl bromide[a] | 5 | dimethylformamide | 279–281 (dec.) |
| 4 | 3-carbomethoxyphenyl | 3-carbomethoxybenzyl bromide[b] | 16 | dimethylformamide | 261.5–264 |
| 5 | 3-isopropylphenyl | 3-isopropylbenzyl bromide[a] | 21 | methanol | 213–215 |
| 6 | 4-carboisopropyloxy-phenyl | 4-carboisopropyloxy-benzyl bromide[b] | 18 | isopropanol | 236–240 |
| 7 | 4-carbo-2-pentyloxy-phenyl | 4-carbo-2-pentyloxy-benzyl bromide[b] | 16 | dimethylformamide | 233–235 |
| 8 | 4-carbomethoxyphenyl | 4-carbomethoxybenzyl bromide[b] | 5.5 | dimethylformamide | 232–235 |

[a]This bromide is prepared from the corresponding methyl ether by treatment with hydrogen bromide
[b]This ester is prepared for the corresponding acyl bromide by treatment with the appropriate alcohol.

EXAMPLE 9

7-[(4-Hydroxyphenyl)methyl]-7H-pyrrolo[3,2-f]quinazoline-1,3-diamine

Treat a suspension of 3.2 g. of 7-[(4-methoxyphenyl)methyl]-7H-pyrrolo[3,2-f]quinazoline-1,3-diamine in 100 ml of methylene chloride at −5° C. with 34 ml. of 0.92 M boron tribromide in methylene chloride. Keep the reaction at 20° C. for 18 hours and dilute with 100 ml. of water. Filter the resulting precipitate, stir in an aqueous potassium carbonate solution, filter, wash with water and dry. Crystallize the precipitate twice from methanol and once from dimethylformamide to obtain 0.63 g. of the title product, m.p. 292° C. (dec.), NMR (dDMSO): δ 5.33 (singlet, N—CH$_2$—C$_6$H$_5$O), 6.67 (doublet, J=9 Hz, 5H), 6.72 (doublet, J=3 Hz, 9H), 7.51 (doublet, J=3 Hz, 8H), 7.75 (doublet, J=9 Hz, 6H) p.p.m.

Analysis for: C$_{17}$H$_{15}$N$_5$O.1/2 dimethylformamide. Calculated: C, 64.99; H, 5.46; N, 22.53. Found: C, 64.98; H, 5.33; N, 22.51.

EXAMPLE 10

7-(4-Pyridinyl)-7H-pyrrolo-[3,2-f]quinazoline-1,3-diamine

A solution of 7.97 g. of 7H-pyrrolo[3,2-f]quinazoline-1,3-diamine in 500 ml. of dry dimethylformamide is stirred, under nitrogen, with 4.61 g. ca. 50% sodium hydride-mineral oil dispersion for 1.5 hours. Addition of 8.95 g. of p-bromopyridine hydrochloride is followed by heating of the reaction mixture at 110° C. for 5 hours. Glacial acetic acid (10 ml) is added and the solvent is removed in vacuo. The residue is stirred thoroughly with a mixture of excess aqueous potassium carbonate solution and 100 ml. of 1 N sodium hydroxide solution, collected, washed with water and dried. Three crystallizations from methanol and one from dimethylformamide and drying afford 0.61 g. of the title product, m.p. 328.5°–329.5° C., NMR (dDMSO): δ 7.16 (doublet, J=8 Hz, 5H), 7.22 (doublet, J=3 Hz, 9H), 7.88 (doublet, J=3 Hz, 8H), 7.96 (doublet, J=8 cps, 6H) p.p.m λ$_{max}^{95\% EtOH}$ 255 mμ (22,900) and 297 mμ (22,100).

Analysis for: C$_{15}$H$_{12}$N$_6$. Calculated: C, 65.20; H, 4.38; N, 30.42. Found: C, 65.34; H, 4.67; N, 30.50.

EXAMPLES 11–13

Employing conditions similar to those recorded in Example 10, 7-H-pyrrolo[3,2-f]quinazoline-1,3-diamine, in dimethylformamide, is converted to the sodium salt with ca. 50% sodium hydride-mineral oil dispersion. The salt is treated with the indicated halide for the period and at the temperature noted to provide the 7-substituted-7H-pyrrolo[3,2-f]quinazoline-1,3-diamines described in Table II.

TABLE II

7-(Substituted)-7H-pyrrolo[3,2-f]quinazoline-1,3-diamines

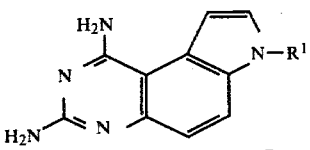

| Example No. | R$^1$ | Alkylating Agent | Reax. Time (°C.) | Reax. Time (hours) | Recryst. Solv. | m.p., °C. |
|---|---|---|---|---|---|---|
| 11 | 2-(4-methylpyridinyl) | 2-fluoro-4-methyl-pyridine | 135 | 4 | methanol | 263–264 |
| 12 | 4-trifluoromethyl-phenyl | p-fluorobenzotri-fluoride | 110 | 6 | methanol | 272.5–273 |
| 13 | 4-carbamoylphenyl | p-fluorobenzamide | 110 | 5.5 | DMSO/water | 333.5–334.5 (dec.) |

EXAMPLE 14

The ability of the compounds of Formula I to inhibit the growth of bacteria in vitro is demonstrated in the following test procedure:

The in vitro antibacterial activities of compounds of the invention are set forth in Tables III and IV below which set forth the MIC values of various compounds when tested according to the above-described procedure:

TABLE III

In vitro Antibacterial Activity of 7-Substituted Methyl-7H-Pyrrolo[3,2-f]Quinazoline-1,3-Diamines

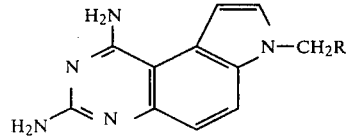

| | | MIC (γ/ml.) | | | | | | |
|---|---|---|---|---|---|---|---|---|
| Compound of Example | R | S. aureus Smith | S. aureus 53-180 | N. catarrhalis 8193 | E. coli 9637 | S. paratyphi 11737 | K. pneumoniae 10031 | P. vulgaris 6896 |
| 2 | 2,4-dichlorophenyl | 0.976 | 0.488 | 0.0038 | 3.9 | 31.3 | 0.488 | — |
| 3 | 3-acetylphenyl | 0.122 | 0.061 | — | 0.244 | 0.976 | 0.031 | 3.9 |
| 4 | 3-carbomethoxyphenyl | 0.976 | 0.122 | — | 1.95 | 31.3 | 0.244 | 125 |
| 5 | 3-isopropyloxyphenyl | 1.95 | 0.488 | 3.9 | 7.81 | 31.3 | 0.244 | 62.5 |
| 6 | 4-carboisopropyloxyphenyl | 0.488 | 0.488 | 0.122 | 15.6 | 62.5 | 0.488 | 125 |
| 7 | 4-carbo-2-pentyloxyphenyl | 15.6 | 7.81 | 7.81 | — | — | 15.6 | — |
| 8 | 4-carbomethoxyphenyl | 31.5 | 7.81 | — | 62.5 | 250 | 15.6 | 250 |
| 9 | 4-hydroxyphenyl | 0.488 | 0.488 | — | 0.976 | 3.90 | 0.244 | 250 |

TABLE IV

In vitro Antibacterial Activity of 7-Substituted-7H-Pyrrolo[3,2-f]Quinazoline-1,3-Diamines

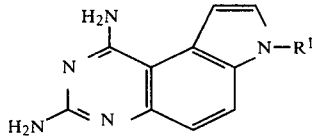

| | | MIC (γ/ml.) | | | | | | |
|---|---|---|---|---|---|---|---|---|
| Compound of Example | $R^1$ | S. aureus Smith | S. aureus 53-180 | N. catarrhalis 8193 | E. coli 9637 | S. paratyphi 11737 | K. pneumoniae 10031 | P. vulgaris 6896 |
| 10 | 4-pyridinyl | 0.448 | 0.224 | 0.0152 | 0.244 | 0.976 | 0.976 | 62.5 |
| 11 | 2-(4-methylpyridinyl) | 3.90 | 0.976 | 0.0152 | 3.9 | 7.81 | 0.244 | 15.6 |
| 12 | 4-trifluoromethylphenyl | 31.3 | 31.3 | — | 250 | — | 3.9 | — |
| 13 | 4-carbamoylphenyl | 1.95 | 7.81 | — | — | — | 0.976 | — |

A stock solution or suspension of the test compound at a concentration of 2500 μg/ml. is prepared utilizing a suitable solvent or medium such as aqueous sodium hydroxide, aqueous lactic acid, methyl cellosolve, dimethylsulfoxide, dimethylacetamide, ethylene glycol, dimethylformamide, formamide, propylene glycol, acetone or methanol. Two-fold dilutions are made by adding appropriate amounts of sterile water to the solution or suspension of the test substance. One ml. quantities of each dilution are incorporated into Wellcotest Sensitivity Test Agar fortified with 5% hemolyzed horse blood (9 ml. vol.) in sterile Petri dishes to give plates containing varying concentrations of the test compound. The hardened surfaces of each plate are incubated with the test organism, and the plates are incubated for 18 hours at 35° C. The in vitro antibacterial activity of the compounds tested is expressed as the "minimal inhibitory concentration" (MIC) which is defined as the least amount of material (μg/ml.) that completely inhibits the test organism.

EXAMPLE 15

The ability of compounds of this invention to demonstrate synergistic action against anti-bacterial infections in mice when administered with sulfomethoxazole is demonstrated in the following test procedure:

The test agent is weighed, suspended in 0.5% aqueous carboxymethyl cellulose, hemogenized (glass tissue grinder) and diluted according to the design of the experiment. Mice (male, 18±1 g., CD-1 strain) are preweighed, pooled, infected at random intraperitoneally with a 0.5 ml. standardized suspension ($LD_{95} \pm 5\%$) of the bacterial organism in 5% gastric mucin and treated at random with single doses of the test agents either at the time of infection or six hours after infecting. The treated groups consist of ten mice per dosage level. Deaths are recorded daily for 14 days and the $PD_{50}$ (mice are treated at time of infection) and $CD_{50}$ (mice are treated six hours after infecting) values are calculated by the method of Reed and Muench [Amer. J. Hyg., 27, (1938)].

TABLE V

In vivo Antibacterial Synergism Data (Mouse) for 7-(4-Pyridinyl)-7H-Pyrrolo[3,2-f]Quinazoline-1,3-Diamine

[Structure of 7-(4-Pyridinyl)-7H-Pyrrolo[3,2-f]Quinazoline-1,3-Diamine]

$PD_{50}{}^a$ Values, mg. per kg., p.o.

| Organism | Cpd. | SM[b] | SM/Cpd. |
|---|---|---|---|
| *Escherichia coli* (E-2) | >400 | 25 | 5.25/1.20 |
| *Escherichia coli* (E-3) | 312.8 | 28.1 | 12.5/6.25 |
| *Staphylococcus aureus* CHP | >400 | 259.4 | 50/7.28 |

[a]This value is the dose required to protect half of the mice from death when the mice are treated immediately after infecting.
[b]SM = sulfomethoxazole

What is claimed is:

1. A compound of the general formula:

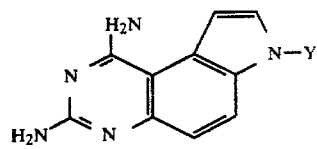

or a non-toxic acid addition salt thereof, wherein:
Y is —CH$_2$R or —R$^1$
wherein:
R is 4-hydroxyphenyl;
and
R$^1$ is 4-carbamoylphenyl.

2. The compound as defined in claim 1 wherein R is 4-hydroxyphenyl.

3. The compound as defined in claim 1 wherein R$^1$ is 4-carbamoylphenyl.

* * * * *